(12) United States Patent
Min et al.

(10) Patent No.: US 8,448,992 B2
(45) Date of Patent: May 28, 2013

(54) STERILE DOCKING DEVICE, MEDICAL FLUID FLOW SYSTEM WITH STERILE DOCKING DEVICE AND METHOD OF USING SAME

(75) Inventors: Kyungyoon Min, Kildeer, IL (US); William H. Cork, Lake Bluff, IL (US)

(73) Assignee: Fenwal, Inc., Lake Zurich, IL (US)

( * ) Notice: Subject to any disclaimer, the term of this patent is extended or adjusted under 35 U.S.C. 154(b) by 184 days.

(21) Appl. No.: 13/028,372

(22) Filed: Feb. 16, 2011

(65) Prior Publication Data

US 2012/0204990 A1   Aug. 16, 2012

(51) Int. Cl.
*F16L 35/00*   (2006.01)
*B32B 38/04*   (2006.01)

(52) U.S. Cl.
USPC ............ 285/3; 285/21.2; 604/905; 156/272.2

(58) Field of Classification Search
USPC ........... 285/3, 4, 21.2; 250/432 R; 156/272.2, 156/304.6; 604/905
See application file for complete search history.

(56) References Cited

U.S. PATENT DOCUMENTS

| | | | | |
|---|---|---|---|---|
| 3,968,195 | A | * | 7/1976 | Bishop ........................ 156/304.6 |
| 4,022,205 | A | * | 5/1977 | Tenczar ........................ 285/21.2 |
| 4,030,494 | A | | 6/1977 | Tenczar |
| 4,157,723 | A | | 6/1979 | Granzow et al. |
| 4,187,846 | A | * | 2/1980 | Lolachi et al. ..................... 285/3 |
| 4,340,097 | A | * | 7/1982 | Ammann et al. .................. 285/3 |
| 4,356,394 | A | * | 10/1982 | Cobean et al. ................. 250/347 |
| 4,369,779 | A | | 1/1983 | Spencer |
| 4,434,822 | A | * | 3/1984 | Bellamy et al. .................. 141/98 |
| RE32,056 | E | * | 12/1985 | Granzow et al. ............ 156/272.2 |
| 4,611,643 | A | * | 9/1986 | Beebe et al. ..................... 604/905 |
| 4,673,400 | A | | 6/1987 | Martin |
| 4,753,697 | A | | 6/1988 | Shaposka et al. |
| 4,770,735 | A | | 9/1988 | Shaposka et al. |
| 4,786,286 | A | * | 11/1988 | Cerny et al. .................... 604/905 |
| 4,793,880 | A | | 12/1988 | Shaposka et al. |
| 4,816,221 | A | * | 3/1989 | Harvey et al. ................. 604/905 |
| 4,828,557 | A | * | 5/1989 | Persidsky ....................... 604/408 |
| 4,832,773 | A | | 5/1989 | Shaposka et al. |
| 4,864,101 | A | | 9/1989 | Shaposka et al. |

(Continued)

FOREIGN PATENT DOCUMENTS

| | | |
|---|---|---|
| EP | 0507321 B1 | 10/1992 |
| JP | 61290035 | 12/1986 |

(Continued)

OTHER PUBLICATIONS

Notification of Transmittal of the International Search Report and the Written Opinion of the International Authority, or the Declaration for PCT/IB2012/000387 dated Jun. 13, 2012.

*Primary Examiner* — David E Bochna
(74) *Attorney, Agent, or Firm* — Cook Alex Ltd.

(57) ABSTRACT

Method and apparatus are disclosed for forming a sealed communication between conduits or conduit subassemblies, each of which has a wall with an exterior surface, and at least one of the walls includes an electrically conductive portion. The exterior surfaces may be brought into a facing relationship, and each conductive portion is heated sufficiently to sterilize the exterior surfaces of the walls by generating electrical current in the conductive portion, such as by application of a voltage or by induction. An aperture is then provided, as by an aperture-forming member, through the facing walls to provide communication between the conduits or conduit subassemblies.

21 Claims, 4 Drawing Sheets

U.S. PATENT DOCUMENTS

| | | | |
|---|---|---|---|
| 4,897,138 A | 1/1990 | Shaposka et al. | |
| 4,913,756 A | 4/1990 | Shaposka et al. | |
| 4,933,036 A | 6/1990 | Shaposka et al. | |
| 5,009,645 A | 4/1991 | Silver et al. | |
| 5,141,592 A | 8/1992 | Shaposka et al. | |
| 5,156,701 A | 10/1992 | Spencer et al. | |
| 5,158,630 A | 10/1992 | Shaposka et al. | |
| 5,209,800 A | 5/1993 | Spencer et al. | |
| 5,244,522 A | 9/1993 | Spencer et al. | |
| 5,248,359 A | 9/1993 | Shaposka et al. | |
| 5,256,229 A | 10/1993 | Spencer | |
| 5,256,845 A | 10/1993 | Schippers | |
| 5,272,304 A | 12/1993 | Been et al. | |
| 5,279,685 A | 1/1994 | Ivansons et al. | |
| 5,342,345 A | 8/1994 | Spencer | |
| D355,848 S | 2/1995 | Ivansons et al. | |
| 5,397,425 A | 3/1995 | Ivansons et al. | |
| D357,926 S | 5/1995 | Ivansons et al. | |
| 5,518,575 A | 5/1996 | Watanabe | |
| 5,525,186 A | 6/1996 | Ivansons et al. | |
| 5,632,852 A | 5/1997 | Ivansons et al. | |
| 5,674,333 A | 10/1997 | Spencer | |
| 5,733,268 A | 3/1998 | Spencer | |
| 5,802,689 A | 9/1998 | Sano | |
| 5,855,731 A | 1/1999 | Spencer | |
| 5,871,612 A | 2/1999 | Spencer | |
| 5,919,173 A | 7/1999 | Spencer | |
| 5,928,216 A | 7/1999 | Spencer | |
| 6,020,574 A | 2/2000 | Ivansons | |
| 6,026,882 A | 2/2000 | Yamada et al. | |
| 6,071,690 A | 6/2000 | Spencer | |
| 6,132,833 A | 10/2000 | Spencer | |
| 6,177,652 B1 | 1/2001 | Ivansons | |
| 6,341,637 B1 | 1/2002 | Yamada et al. | |
| 6,348,049 B1 | 2/2002 | Spencer | |
| 6,460,592 B1 | 10/2002 | Sano et al. | |
| 6,463,979 B1 | 10/2002 | Sano et al. | |
| 6,637,489 B1 | 10/2003 | Spencer | |
| 6,705,372 B2 | 3/2004 | Sano et al. | |
| 7,097,209 B2 * | 8/2006 | Unger et al. | 285/3 |
| 7,119,305 B2 | 10/2006 | Sano et al. | |
| 7,223,262 B2 | 5/2007 | Brehm et al. | |
| 7,264,771 B2 * | 9/2007 | Bilstad et al. | 250/453.11 |
| 7,371,305 B2 | 5/2008 | Sano et al. | |
| 7,398,813 B2 | 7/2008 | Ivansons et al. | |
| 7,484,529 B2 | 2/2009 | Yokota et al. | |
| 7,657,996 B2 | 2/2010 | Sano et al. | |
| 7,779,880 B2 | 8/2010 | Sano et al. | |
| 7,828,788 B2 | 11/2010 | Brehm et al. | |
| 7,938,454 B2 * | 5/2011 | Buchanan et al. | 604/905 |
| 7,964,048 B2 | 6/2011 | Hlavinka et al. | |
| 2002/0174956 A1 | 11/2002 | Sano et al. | |
| 2006/0005371 A1 | 1/2006 | Sano et al. | |
| 2006/0054275 A1 | 3/2006 | Sano et al. | |
| 2006/0054613 A1 | 3/2006 | Sano et al. | |
| 2006/0144525 A1 | 7/2006 | Sano et al. | |
| 2007/0142960 A1 | 6/2007 | Bollinger et al. | |
| 2007/0225673 A1 | 9/2007 | Brehm et al. | |
| 2008/0009833 A1 | 1/2008 | Corbin et al. | |
| 2010/0137826 A1 | 6/2010 | Watts et al. | |

FOREIGN PATENT DOCUMENTS

| | | |
|---|---|---|
| JP | 09150458 | 6/1997 |
| WO | WO8202528 | 8/1982 |
| WO | WO2008131442 | 10/2008 |

* cited by examiner

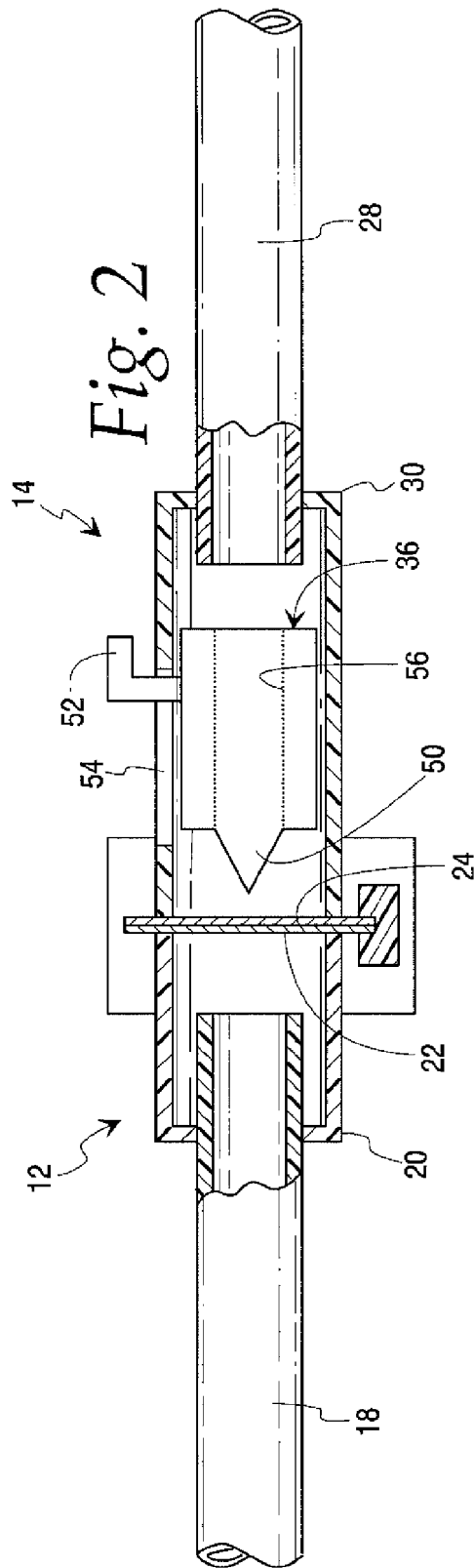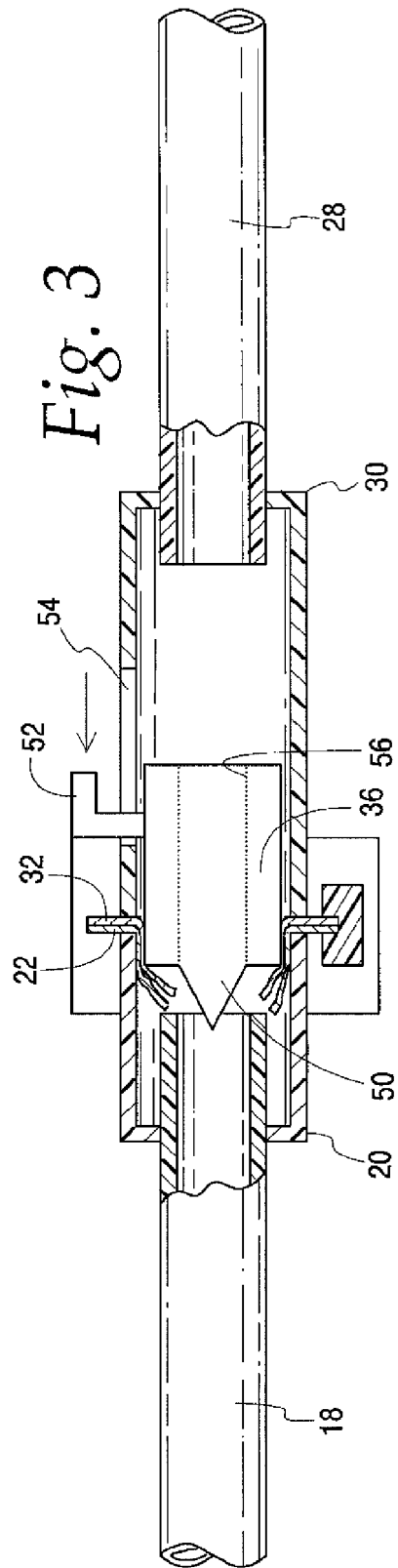

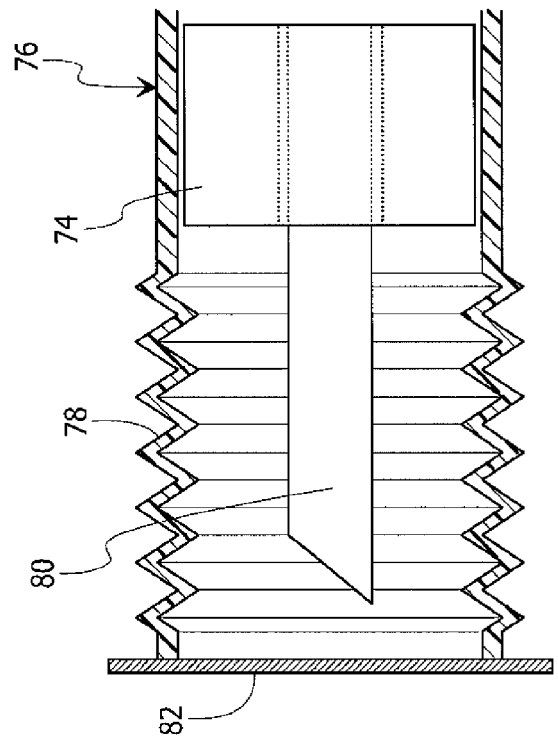
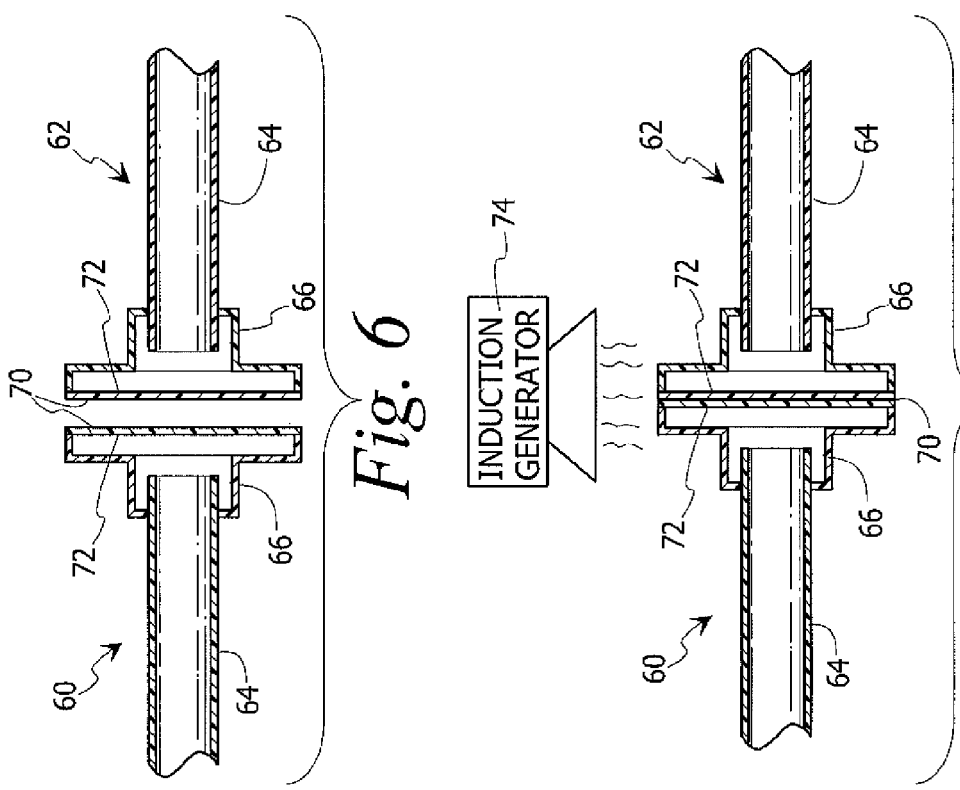

STERILE DOCKING DEVICE, MEDICAL FLUID FLOW SYSTEM WITH STERILE DOCKING DEVICE AND METHOD OF USING SAME

The present disclosure relates generally to sterile docking devices and systems, to medical fluid flow systems employing such devices or systems and related methods of use.

Pre-sterilized disposable medical fluid flow systems are used in a wide variety of medical applications. In many situations these systems are assembled by joining together pre-sterilized subsystems or devices. This is often done using what is referred to a sterile docking device or method to preserve sterility of the assembled system.

Such sterile docking or joining systems may potentially be used in large scale manufacturing of medical fluid flow systems. They may also be used "bedside" or in a pharmacy, blood bank or other setting where the fluid flow system is assembled on a custom, as-needed basis for a particular patient, donor or procedure.

A number of different sterile docketing or joining approaches have been heretofore used. One approach employs a pair of mating members, each having a facing plastic membrane. After the two members are joined, the docking device is exposed to radiant energy, causing the membranes to melt and form a sterile fluid pathway through the device. Such a system is illustrated in U.S. Pat. No. 4,157,723.

Another approach has been disclosed for high volume manufacturing settings for assembling disposable medical fluid flow systems that include one portion (the "wet" portion), which includes a fluid filled container and must be sterilized by one technique, and another portion (the dry portion), which may include empty tubing, flow control members, processing chambers and the like, which is preferably sterilized in other ways. This approach, as described in U.S. Pat. No. 5,009,645, employs an electron beam or the like to sterilize isolated portions of the assembly after they have been joined together. After the isolated regions are joined and sterilized, the isolated regions are opened to allow for direct communication between the "wet" and "dry" portions of the system. The use of e-beam or similar radiation devices, of course, requires a substantial investment in manufacturing equipment as well as additional procedures and safeguards during manufacture.

It is also known to use sterilizing filters on the inlet flow line of a system that couples a pre-sterilized liquid container or the like to a separately pre-sterilized fluid flow tubing system. Such an arrangement is illustrated in U.S. Pat. No. 4,978,446. In that approach, the medical personnel are required to manually join the fluid flow tubing system to the fluid container, such as by spiking the fluid container with a piercing member associated with the fluid flow system.

As shown in U.S. Pat. No. 4,369,779, another sterile docking system employs a thin heated wafer or blade to join plastic tubing by cutting each tube to form a molten end on each tube. The tubes are slid from the wafer into direct contact with each other. As the plastic cools, a weld forms between the tubes. This system, however, requires relatively costly wafers and precise movement of the tubing from the wafer or blade.

Another docking arrangement for medical fluid flow systems employing a filter is described in pending U.S. patent application Ser. No. 12/327,072, filed Dec. 3, 2008 and entitled Pre-Assembled Medical Fluid System And Method Of Using The Same.

Notwithstanding the above sterile docking devices and methods, there remains a need for low cost, efficient and/or easy to use sterile docking devices and systems.

SUMMARY OF DISCLOSED SUBJECT MATTER

Accordingly, the subject matter set forth below is directed to new method and apparatus for forming a sealed communication between conduits. More specifically in accordance with one aspect of the present subject matter a method is described for forming sealed communication between conduits, in which each of the conduits includes a wall having an exterior surface. At least one of the walls includes an electrically conductive portion. The method includes bringing the walls into a facing relationship, heating each conductive portion sufficiently to sterilize the facing exterior surfaces by generating electrical current in the conductive portion, and creating an aperture through the walls to provide communication between the conduits.

In accordance with another aspect of the subject matter, a conduit subassembly is provided for use in making a sealed connection with another conduit subassembly. The conduit subassembly includes a conduit having a wall with an exterior surface. The wall includes an electrically conductive portion and the exterior surface is configured for face-to-face engagement with an exterior surface of another conduit subassembly to provide sealed communication therebetween. The exterior surface of the conduit subassembly is sterlizable by heating resulting when electrical current is generated in the electrically conductive portion.

In accordance with yet another aspect of the subject matter a conduit assembly is provided in which there is sealed communication between first and second conduit subassemblies. Each conduit subassembly includes a wall having an exterior surface and at least one of the walls includes an electrically conductive portion. The exterior surfaces of the subassemblies are disposed in sealed face-to-face relation and are sterilizable by heat from electric current in each conductive portion. An opening member is movable relative to the walls to facilitate opening of an aperture in the walls to provide sealed communication between the first and second conduit subassemblies.

The electrical current may be generated in the conductive portion(s) in different ways, including by direct connection between opposite poles of a generator or by induction. Further, if both walls have conductive portions, they may be connected to an electrical generator in parallel or in series, or electrical current may be generated in both by induction.

DESCRIPTION OF DRAWINGS

Turning now to a more detailed description of the present subject matter, which is shown for purposes of illustration and not limitation in the accompanying drawings, of which:

FIG. 2 is a plan view of a connector portion of FIG. 1, partially in section, showing connecting portions of two conduit subassemblies with exterior wall surfaces in direct sealed face-to-face contact, before fluid conduit subassemblies are placed in sealed communication.

FIG. 3 is a plan view, similar to FIG. 2, illustrating formation of an aperture in facing exterior surfaces of first and second conduit subassemblies often sterilization of the facing surfaces.

FIG. 6 is a cross-sectional view of connecting portions of conduit subassemblies in a position in which exterior surfaces are being brought together in face-to-face relation.

FIG. 7 illustrates the first and second subassemblies of FIG. 6 in which the exterior surfaces are brought together in direct sealed face-to-face contact, and electrical current is induced in a conductive portion at least one and preferably both of the mating surfaces by induction.

FIG. 8 is a cross-sectional view of a connecting portion of a conduit subassembly including an access member fully contained within the subassembly and in which the conduit subassembly is flexible, allowing the access member to be advanced for forming an aperture in the walls after sterilization.

DETAILED DESCRIPTION

Figure 1:
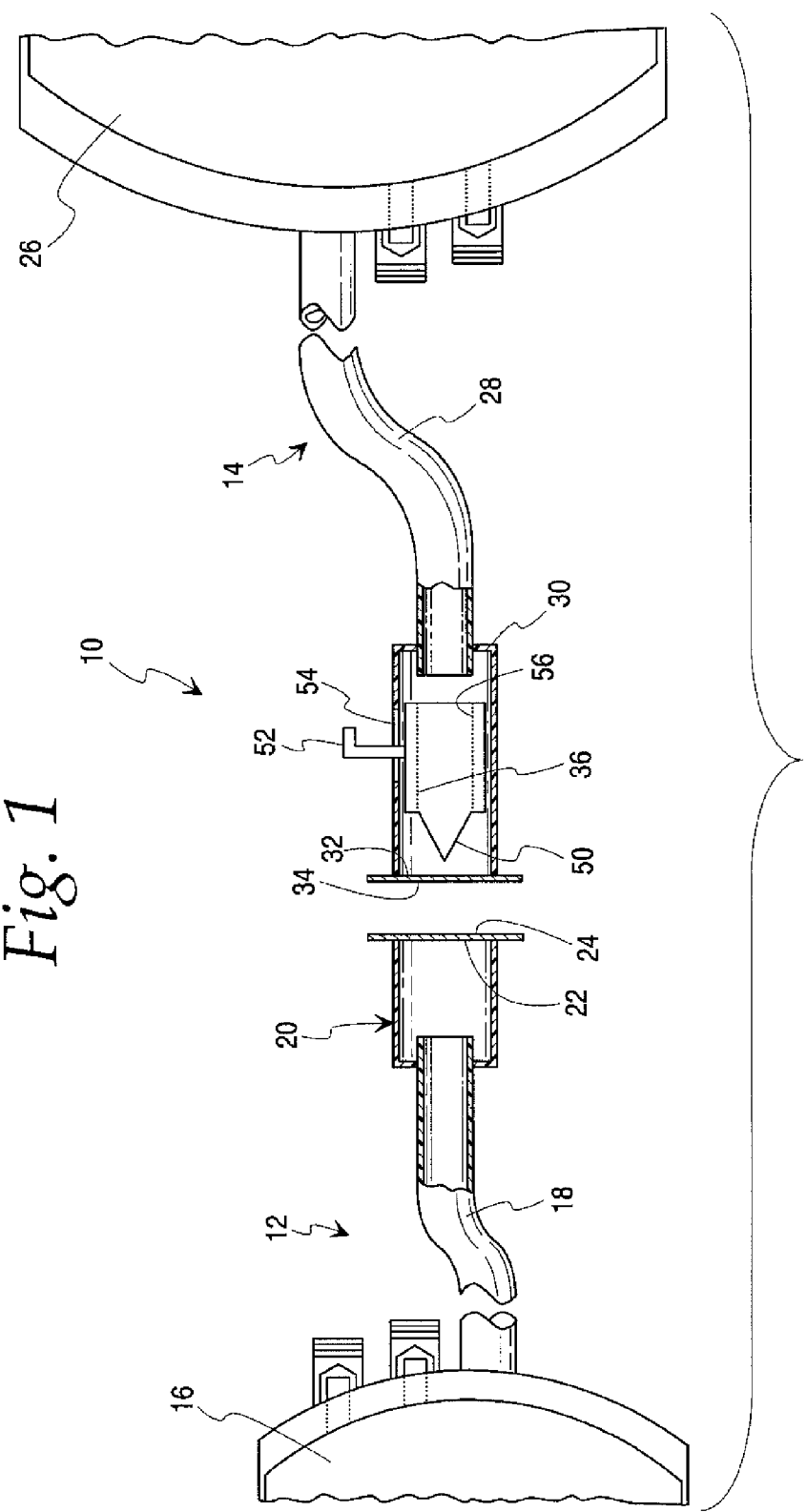
FIG. 1 is a plan view, partially in cross-section, of a disposable medical fluid flow assembly including two conduit subassemblies employing one aspect of the present subject matter.

FIG. 1 illustrates a medical fluid flow conduit assembly 10 made up of at least a first conduit subassembly, generally at 12, and a second conduit assembly, generally at 14. More specifically, the first conduit assembly 12, as shown for purposes of illustration and not limitation, may optionally include one or more medical fluid flow containers or bags 16, and flexible plastic tubing 18 in fluid flow communication at one end with the container or bag 16 and in fluid flow communication at the other end with a housing 20. The housing 20 includes a wall 22 (which may also be referred to as a mating or connecting wall or wall portion) having an exterior surface 24 (which may also be referred to as a mating or connecting surface or surface portion). The second conduit assembly 14, as shown for purposes of illustration, may also optionally include one or more medical fluid containers or bags 26, and flexible plastic tubing 28 in fluid flow communication at one end with the container or bag 26, and in fluid flow communication at the other end with a connection site or housing 30. The housing 30 includes a wall 32 having an exterior surface 34 and aperture forming member 36 that is movably positioned within the housing 30 for forming an aperture through the walls 22 and 24 and their respective exterior surfaces 32 and 34 after sterilization to provide sealed communication as described in more detail below.

Although the subject matter of this description is illustrated with reference to specific figures and specific parts and pieces of the apparatus in those figures, it should be understood that this is for purposes of illustration and not limitation. It is contemplated for example that the subject matter of this application may be used for sealingly joining at least two conduits, preferably but not necessarily presterilized conduits. Those conduits may be, but are not necessarily, part of a medical fluid flow assembly or subassembly, and any such medical fluid flow assembly may include one or more medical fluid containers or bags, but the presence of such containers or bags is not required. Similarly, the conduit subassemblies 12 and 14 are shown with flexible tubing terminating in housings, each of which mounts a wall having an exterior surface for making the sealed connection. The connecting wall, however, does not need to be a part of a housing at the terminal end of flexible tubing. Any suitable structure may employ such connecting walls or wall portions with exterior mating surfaces, and the configuration and location of such walls and surfaces are not limited to the particular configurations shown. In addition there may be additional tubing, containers, flow control devices such as clamps or frangible connectors, venous access devices such as needles, filters, blood separation chambers or devices within each of the first and second conduit subassemblies. Additional subassemblies may also be employed with added connection sites.

As illustrated in more detail in FIGS. 2 and 3, the first and second conduit subassemblies 12 and 14 may be brought together with the exterior surfaces 24 and 34 in face-to-face relation, preferably in full, direct, face-to-face contact. At least one and preferably each of the mating walls 22, 32 includes an electrically conductive portion within which electrical current may be generated. In the figures illustrated, the entire walls 22 and 32 are conductive, as each is preferably made of a single thickness of electrically conductive material such as metallic foil. Other wall constructions, however, may be used. The mating walls may be, for example, laminated with a layer of metal or other conductive material disposed within or on the one or both of the surfaces of the mating wall, including the exterior mating surface. In addition, the mating exterior surface can be substantially non-conductive and include a separate conductive portion disposed on of the exterior surface or within the mating wall. Preferably the walls are sufficiently frangible or weakened in preselected areas to allow an aperture to be created through them.

In any event, after the exterior surfaces of the subassembly walls are brought together in a face-to-face relation, electrical current is generated in the conductive portions of one or both of the walls. The flow of electrical current within the conductive portion, heats the wall and the exterior surface in particular. Sufficient current generated within the conductive portion for a sufficient time period will, via electrical resistance heating for example, heat the external mating surfaces sufficiently to destroy and/or deactivate any microorganisms and, in essence, sterilize the exterior mating surfaces.

The electrical current can be generated within the conductive portion of the mating wall in any suitable manner. For example, electrical current may be generated by connecting the conductive portion of at least one of the mating walls between the opposite terminals of a voltage source such as a DC or AC generator. Where each mating wall has a conductive portions, the conductive portions be connected in parallel or in series between the terminals of a voltage source. In addition, electrical current may be generated by induction as illustrated in FIGS. 6 and 7.

Figure 5:
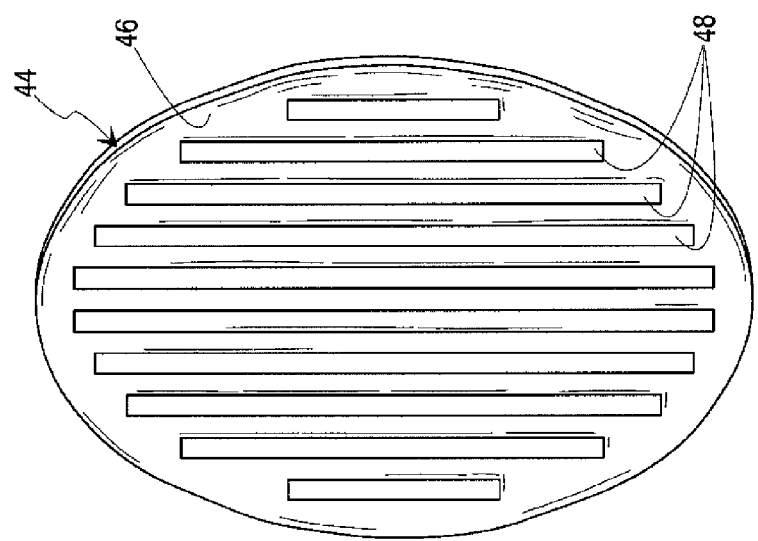
FIG. 5 is a perspective view of another embodiment of a wall including a conductive portion in the form of substantially parallel elongated conductors disposed on the exterior surface.
Figure 4:
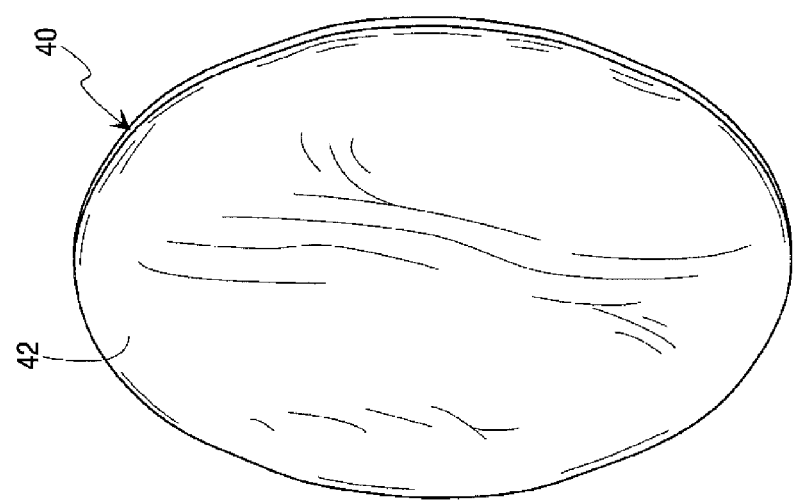
FIG. 4 is a perspective view of one form of mating surface, in which the exterior surface is comprised essentially entirely of a conductive metallic film.

FIGS. 4 and 5 illustrate examples of alternatives for the mating walls 22 or 32. Turning to those figures, FIG. 5 is a perspective view of a mating wall 40 that has an external mating surface 42, and which may be made of a single thickness of conductive material, such as a metal, e.g., aluminum, copper, conductive polymer, a blend of materials or other suitable material or alloy. As mentioned above, the mating wall may have other constructions as well. For example, the wall may be laminated with a conductive layer, such as conductive metallic material or foil, as one of the layers of the laminate. Preferably any such layer extends to the peripheral edges of the mating wall so that it extends to the full peripheral extent of the mating wall.

In another configuration, as shown in FIG. 6, the mating wall 44 has a non-conductive exterior surface 46, and at least one and preferably a plurality of electrical conductors 48 are mounted or carried on the support surface 46. The electrical conductors may be arranged in any suitable configuration. As illustrated in FIG. 6, the electrical conductors may be in the form of substantially elongated, spaced apart, parallel strips 48, having varying length according to the relative location of the strip on the support surface of the mating wall.

Turning back now to FIGS. 2 and 3, whatever the construction of the mating walls 22 and 32, it is preferred that the walls be of a material and configuration sufficiently weak or frangible that an aperture may be formed in the walls by the aperture forming member 36. As shown in FIGS. 2 and 3, for purposes of illustration, the aperture forming member 36 includes a tapered/pointed piercing member 50 extending from the distal end of the aperture forming member 36 within housing 30. The aperture forming member 36 includes an actuator 52 that extends through a slot 54 in the housing, which allows the user to manually advance the aperture forming member to pierce the mating walls and thereby provide direct liquid and or gas flow communication between the first and second conduit subassemblies. As illustrated, the body of the aperture forming member includes an axially extending internal lumen 56 that allows unimpeded fluid flow communication between the conduit subassemblies.

With the configuration thus described above, the subassemblies 12 and 14 may be joined together to provide sealed communication therebetween. Specifically, the external mating surfaces 24 and 34 of walls 22 and 32 are presented in facing relationship. Preferably the facing surfaces are sealed from ambient contaminating conditions by their direct contact, although the housings may be configured to enclose the facing surfaces within a closed or sealed region to prevent external contamination after sterilization. By generating electrical current in a conductive portion of at least one, and preferably both, of the mating walls, the facing exterior surfaces may be heated and sterilized. An aperture may then be provided through the mating walls, to provide sealed, fluid flow communication between first and second conduit subassemblies.

As described above, the exterior surfaces 24 and 34 of the mating walls 22 and 32, which are in face-to-face relation, are heated to sterilizing temperature by generating electrical current in the conductive wall portion(s). However, the present subject matter is not limited to a device in which electrical current is generated by connecting the conductive portions to opposite terminals of a voltage source. In addition, electrical current may be generated by other suitable means such as induction, and the conductive portion may be of any material in which electrical current (e.g., eddy current) may be generated by induction.

FIGS. 7 and 8 illustrate an induction heating arrangement. As shown there, first and second conduit subassemblies 60 and 62 are preferably each pre-sterilized, for example by gamma, steam or other suitable sterilization process. Each conduit subassembly includes, as illustrated, a tubing portion 64 and a housing portion 66, each housing having a mating wall 72 with an exterior mating surface 70. The mating surfaces are generally flat and planar, and are brought together in full, direct face-to-face contact as shown in FIG. 8.

The mating walls 72 are comprised entirely or at least partially of a conductive portion of a material in which current, such as eddy current, may be generated by induction in a manner well known in the electrical field. More specifically, the contacting surfaces 70 are mounted in sufficient proximity to an induction generator 74 that electrical current may be generated within at least one and preferably both of the mating walls 72 to heat the walls and the mating surfaces 70 of the walls, raising the temperature sufficiently to sterilize the exterior facing surfaces 70 of the mating wall portions. After the exterior facing surfaces 70 are sterilized, and while they remain in direct contact, free of ambient contamination, an aperture is preferably formed in any suitable manner through the walls, so as to join the first and second conduit subassemblies in a sealed manner so that sterility is preserved. Any appropriate aperture forming member may be employed. The housings 66, as in the earlier embodiment, remain joined by any appropriate means, such as heat sealing, mechanical bond or attachment, so as to maintain the exterior mating surfaces in a sealed environment, not subject to external contamination after sterilization. Although the mating surfaces shown in prior figures are in direct face-to-face contact along essentially the full area of the mating surfaces, that relationship is not absolutely required. For example, the peripheral edges only of the mating surfaces may be in direct, sealed contact and the remainder of the surfaces be spaced apart. The peripheral edge seal would prevent ambient contamination of the mating surfaces after they are sterilized.

FIG. 9 illustrates an alternative aperture forming member 74 that may be housed fully within one of the conduit subassemblies. The illustrated subassembly has a wall 76 that is flexible, such as by an accordion or bellows configuration, which allows the aperture forming member 74 to be actuated by exterior flexing of the wall. With a bellows wall, the hollow piercing member 80 may be forced through the respective mating wall 82 by external manipulation compressing the accordion or bellows wall portion of the subassembly, and no external access or actuation member is required.

Although the subject matter herein has been described with reference to specific figures, it is understood that many variations and configurations are possible. Accordingly, the scope hereof is not limited to the specific form illustrated, but is as defined in the following claims.

The invention claimed is:

1. A method of forming a sealed communication between conduit subassemblies, each conduit subassembly including a housing mounting a wall having an exterior surface, at least one of the exterior surfaces comprising a non-conductive support surface and an electrically conductive member carried by the support surface and the electrically conductive member that comprising a layer of conductive material extending substantially co-extensive with the exterior surface, which method comprises:
   bringing the exterior surfaces into a facing contacting relationship,
   heating each conductive portion sufficiently to sterilize the exterior surfaces by generating electrical current in the conductive portion, and
   after sterilizing creating an aperture through the walls to provide communication between the conduits.

2. The method of claim 1 in which at least one of the exterior surfaces is of electrically conductive material.

3. The method of claim 1 in which at least one of the walls is defined by a single layer of conductive material.

4. The method of claim 1 in which an aperture is created in at least one of the walls by operating an aperture-forming member that is disposed within at least one of the subassemblies and is operable to create an aperture in at least one of the walls.

5. The method of claim 1 in which a piercing member is operably located within at least one of the conduit subassemblies and the conduit subassembly is sufficiently flexible to allow the piercing member to be moved to pierce at least one of the walls by flexing the conduit subassembly by external manipulation.

6. The method of claim 1 in which electrical current is generated by connecting each electrically conductive portion between opposite terminals of an electrical voltage source or by induction.

7. The method of claim 1 in which each of the walls includes an electrically conductive portion configured to heat the respective wall surface sufficiently to sterilize the exterior wall surface when electrical is generated in the conductive portion.

8. A conduit subassembly for use in making a sealed connection with another conduit subassembly, the conduit subassembly including a conduit having a housing mounting a wall with an exterior surface, the exterior surface comprising a non-conductive support surface and an electrically conductive member carried by the support surface, the electrically conductive member comprising a layer of conductive material extending substantially co-extensive with the exterior surface, the exterior surface being configured for contacting face-to-face engagement with an exterior surface of another conduit subassembly to provide sealed communication therebetween, the exterior surface of the conduit subassembly being sterilizable by heating of the conductive portion resulting from electrical current therein.

9. The conduit subassembly of claim 8 in which the wall is defined by a single layer of conductive material.

10. The conduit subassembly of claim 8 in which the wall is defined by a single layer of electrically conductive metallic foil.

11. The conduit subassembly of claim 8 further comprising an aperture-forming member movably disposed within the conduit subassembly, for forming an aperture in the wall.

12. The conduit subassembly of claim 11 in which the housing includes a compressible wall portion associated with the aperture forming member.

13. A conduit assembly providing sealed communication between first and second conduit subassemblies, each conduit subassembly mounting a wall having an exterior surface, and at least one of the walls including a conductive portion that comprises a layer of conductive material extending substantially co-extensive with the exterior surface, the exterior surfaces being disposed in sealed contacting face-to-face relation and being sterilizable by heat from electric current in the conductive portion, and an opening member movable relative to the walls to facilitate the opening of an aperture in the walls to provide sealed communication through the walls between the first and second conduit subassemblies.

14. The conduit assembly of claim 13 in which the wall of at least one subassembly comprises an electrically conductive metallic material.

15. The conduit assembly claim 13 further comprising an aperture-forming member movably disposed within at least one of the conduit subassemblies.

16. The conduit assembly of claim 15 including a housing configured to allow external manual manipulation of the housing to actuate the aperture-forming member to form an aperture in the exterior surface of the housing.

17. The conduit assembly of claim 13 in which the electrically conductive portion comprises a material in which electrical current may be generated by induction or by connecting the conductive portion between opposite terminals of an electrical voltage source.

18. A method of forming a sealed communication between conduits, each conduit including a wall having an exterior surface and at least one of the walls including an electrically conductive portion, a piercing member being operably located within at least one of the conduits and the conduit being sufficiently flexible to allow the piercing member to be moved to pierce at least one of the walls by flexing the conduit by external manipulation, which method comprises:
  bringing the exterior surfaces into a facing relationship,
  heating each conductive portion sufficiently to sterilize the exterior surfaces by generating electrical current in the conductive portion, and
  creating an aperture through the walls to provide communication between the conduits.

19. A conduit subassembly for use in making a sealed connection with another conduit subassembly, the conduit subassembly including a conduit having a wall with an exterior surface, which wall includes an electrically conductive portion, the exterior surface being configured for face-to-face engagement with an exterior surface of another conduit subassembly to provide sealed communication therebetween, the exterior surface of the conduit subassembly being sterilizable by heating of the conductive portion resulting from electrical current therein and an aperture-forming member movably disposed within the conduit subassembly for forming an aperture in the wall, the housing including a flexible wall portion associated with the aperture forming member.

20. A method of forming a sealed communication between conduits, each conduit including a wall having an exterior surface and at least one of the walls including an electrically conductive portion, and an aperture-forming member disposed within at least one of the conduits and operable to create an aperture in at least one of the walls, the method comprises:
  bringing the exterior surfaces into a facing relationship;
  heating each conductive portion sufficiently to sterilize the exterior surfaces by generating electrical current in the conductive portion; and
  creating an aperture through the walls to provide communication between the conduits.

21. A conduit subassembly for use in making a sealed connection with another conduit subassembly, the conduit subassembly including a conduit having a wall with an exterior surface, which wall includes an electrically conductive portion, the exterior surface being configured for face-to-face engagement with an exterior surface of another conduit subassembly to provide sealed communication therebetween, the exterior surface of the conduit subassembly being sterilizable by heating of the conductive portion resulting from electrical current therein and an aperture-forming member movably disposed within the conduit subassembly for forming an aperture in the wall.

* * * * *